United States Patent
Luther et al.

(10) Patent No.: US 7,466,400 B2
(45) Date of Patent: Dec. 16, 2008

(54) DEVICE AND METHOD FOR AUTOMATICALLY DETECTING AT LEAST ONE FLUORESCENT AND/OR LIGHT ABSORBING INDICATOR CONTAINED IN A LIQUID SERVICE FLUID DURING THE PROCESS OF FILLING THE SERVICE FLUID INTO A MACHINE

(75) Inventors: Rolf Luther, Speyer (DE); Christian Seyfert, Mannheim (DE); Fritz Stumm, Heidelberg (DE)

(73) Assignee: Fuchs Petrolub AG, Mannheim (DE)

( * ) Notice: Subject to any disclaimer, the term of this patent is extended or adjusted under 35 U.S.C. 154(b) by 323 days.

(21) Appl. No.: 10/559,552

(22) PCT Filed: May 25, 2004

(86) PCT No.: PCT/EP2004/005603

§ 371 (c)(1),
(2), (4) Date: Aug. 31, 2006

(87) PCT Pub. No.: WO2004/109265

PCT Pub. Date: Dec. 16, 2004

(65) Prior Publication Data

US 2007/0064323 A1   Mar. 22, 2007

(30) Foreign Application Priority Data

Jun. 4, 2003  (DE) ................................ 103 25 537

(51) Int. Cl.
*G01N 33/28* (2006.01)
(52) U.S. Cl. ...................................................... 356/70
(58) Field of Classification Search ........................ None
See application file for complete search history.

(56) References Cited

U.S. PATENT DOCUMENTS

| | | | |
|---|---|---|---|
| 5,225,679 A | 7/1993 | Clarke et al. | 250/343 |
| 5,729,967 A | 3/1998 | Joos et al. | 60/390.06 |
| 5,928,954 A | 7/1999 | Rutledge et al. | 436/56 |
| 5,958,780 A | 9/1999 | Asher et al. | 436/56 |
| 6,193,710 B1 | 2/2001 | Lemberg | 606/5 |
| 6,274,381 B1 | 8/2001 | Pauls et al. | 436/56 |

FOREIGN PATENT DOCUMENTS

| | | |
|---|---|---|
| DE | 100 53 069 | 5/2002 |
| DE | 697 12 218 T2 | 10/2002 |
| EP | 1 054 251 | 11/2000 |
| EP | 0 935 750 | 4/2002 |
| WO | WO 94/12874 | 6/1994 |

*Primary Examiner*—Gregory J Toatley, Jr.
*Assistant Examiner*—Amanda H Merlino
(74) *Attorney, Agent, or Firm*—Davidson, Davidson & Kappel, LLC

(57) ABSTRACT

A method and a device for the automatic detection of at least one fluorescent and/or light-absorbent indicator contained in a liquid service fluid during the filling of a machine, in particular a combustion engine of a vehicle, with said service fluid are provided. Detection takes place in the following manner: irradiation during the filling of the service fluid to be analyzed using at least one light source (3) in a measuring section (2); capture of the light (14) passing through the service fluid in the measuring section (2) and/or emanating from the indicator contained in said fluid as a result of a fluorescent effect, by means of a light collector (5), the intensity of the light being influenced by the indicator or indicators or the concentration thereof; generation of at least one measurement signal (8, 9) representing the intensity of the light that strikes.

20 Claims, 2 Drawing Sheets

DEVICE AND METHOD FOR AUTOMATICALLY DETECTING AT LEAST ONE FLUORESCENT AND/OR LIGHT ABSORBING INDICATOR CONTAINED IN A LIQUID SERVICE FLUID DURING THE PROCESS OF FILLING THE SERVICE FLUID INTO A MACHINE

The present invention relates to a device and to a method for automatically detecting at least one fluorescing and/or light-absorbing indicator contained in a liquid service fluid during the process of filling the service fluid into a machine.

BACKGROUND

Within the meaning of the present Application, liquid service fluids are understood to include, in particular, lubricating oil, engine oil, hydraulic oil and other such service fluids.

To optimize the service life of machines, it is increasingly vitally important to select the proper service fluids for the machines, such as, in particular, lubricating oil for combustion engines. Under certain circumstances, unsuitable oil can lead to immediate failure of the machine, while an especially high-grade lubricating oil can ensure an above average operational life. During a manual filling operation, when changing or replenishing oil, errors caused by the inadvertent selection of an inappropriate lubricating oil cannot be ruled out. This is becoming ever more critical, since, to an increasing degree, motor vehicle engines require lubricating oils that are tailored and adapted to the specific engine type, for example. If an inappropriate service fluid is poured in, and this is not detected in time, substantial adverse consequences, such as premature failure of the machine, may arise.

In addition, the quality of a service fluid is decisive for determining its replacement interval. Today's motor vehicles do, in fact, already come equipped with on-board computers which calculate or adjust the oil replacement intervals as a function of various operating parameters. However, it is not possible to automatically consider the quality of the lubricating oil that has been poured in.

Dyes for marking fuels are already known from the patent literature. Thus, U.S. Pat. No. 6,274,381 B1 discusses using two or more visible dyes, whose absorption maxima are at distinct wavelengths from each other, in a fuel. By introducing a sample of such a marked fuel into a suitable laboratory apparatus, it is possible to identify the indicator. To this end, U.S. Pat. No. 6,274,381 B1 discusses using a light source and determining the absorption characteristic of the indicators.

Another method is known from U.S. Pat. No. 5,928,954. This document describes using fluorescing dye in the liquid to be marked. The indicator is detected in a laboratory apparatus which includes a sample holder into which a small amount of the substance to be investigated is introduced. The sample is then irradiated by laser diodes, and the fluorescence produced by the fluorescing dye is measured.

Another fluorescing dye for fuels is known from U.S. Pat. No. 5,729,967.

SUMMARY OF THE INVENTION

An object of the present invention is to make it possible for the identity of a service fluid contained in a machine to be automatically detected.

The present invention provides a device for automatically detecting at least one fluorescing and/or light-absorbing indicator contained in a liquid service fluid during the process of filling the service fluid into a machine, in particular into the engine of a vehicle, having a filler tube for the service fluid, through which the service fluid to be poured in reaches the machine's service fluid supply, a measurement section made of a translucent material which is at least partially filled with or traversed by the flow of the service fluid when filling the same into the filler tube, having at least one light source, which radiates onto the measurement section, an opto-receiver, onto which the light impinges that is transmitted through the service fluid when the service fluid flows through the measurement section and/or emanates from the indicator due to a fluorescent effect, and which generates a measurement signal as a function of the intensity of the light impinging on the opto-receiver, and having an evaluation unit, in which the at least one measurement signal of the opto-receiver is evaluated.

The design according to the present invention makes it possible, for the first time, to automatically ascertain a liquid service fluid, in particular its identity or quality, when filling the same into a machine.

It was discovered in accordance with the present invention that the service fluids typically employed have regions of distinctly reduced absorption in their absorption spectrum. With regard to lubricating oils, it was established that no absorption or only diminished absorption occurs in the 500 to 1000 nm region, so that these regions, in particular, lend themselves to marking by indicators. In the region above 500 nm, the fluorescence indicators are easily excited, since the exciting light is not absorbed or is hardly absorbed by the service fluid. The light emitted by the fluorescence indicator may likewise be sensed very easily in the region above 500 nm, since the absorption of the service fluid does not influence or only slightly influences the measuring result.

In accordance with the present invention, dyes, in particular fluorescing dyes may be added as indicators to the service fluid. The device according to the present invention is able to automatically detect such dyes when the service fluid is filled into the machine. Accordingly, in addition to a filler tube for the service fluid, the device according to the present invention has a measurement section made of a translucent material which is at least partially filled with or traversed by the flow of the service fluid when filling the same into the machine. The light source and the opto-receiver may be used to measure the indicator(s) and concentrations thereof. The measurement signal derived therefrom is then further processed by an evaluation unit. The measurement signals may be compared to data stored in an evaluation matrix in advance, for example, in order to obtain information on the service fluid that has been filled into the machine. This information may then be automatically utilized further, for example to calculate a replacement interval for the service fluid that is adapted to the quality of the service fluid that was poured in.

One advantageous embodiment provides for the opto-receiver to have at least two light sensors, whose frequency regions are distinct from one another, and which each generate one measurement signal. Thus, a plurality of indicators may be measured by the device according to the present invention. In addition, taking into consideration that different concentration thresholds of the indicators may be determined in accordance with the present invention, a multiplicity of encoding options is derived. When two indicators and four concentration levels are used, then 16 encoding options are already derived. When three dyes and four concentration levels are used, this number increases to 64, and when four indicators are used, it climbs to 256.

One advantageous embodiment of the present invention provides for the light source and the opto-receiver to be oriented to the measurement section and positioned at an angle of 0 to 170 degrees around the measurement section. It is especially beneficial when the light source and the opto-receiver are positioned at an angle of 30 to 140, in particular of 60 to 120 degrees. An especially good measurement signal is hereby achieved when using fluorescing dyes.

In accordance with one advantageous embodiment of the present invention, in the direction of flow upstream of the measurement section, the filler tube has a reduced cross-sectional area in the section leading into the measurement section. This reduced cross-sectional area is located in particular above the measurement section, it sufficing when only one partial flow of the fill fluid passes through the measurement section. The advantage of this design is that the reduced cross section ensures that the measurement section is completely filled, thereby providing constant and known measuring conditions.

Moreover, the present invention provides for the measurement section to be designed as a measuring tube that leads directly or indirectly into the machine's service fluid supply.

A further improvement is achieved by providing a plurality of light sources which radiate in frequency regions which are distinct from one another. This facilitates the process of detecting various indicators.

One advantageous embodiment of the present invention provides for the light sources to be constituted of LEDs and/or of laser diodes having different wavelengths.

The present invention also relates to a machine, in particular to the engine of a vehicle having a device including the aforementioned features.

Moreover, the present invention provides for a method for automatically detecting at least one fluorescing and/or light-absorbing indicator contained in a liquid service fluid during the process of filling the service fluid into a machine, in particular into the engine of a vehicle, including the following steps:

irradiating the service fluid to be detected during the filling process by at least one light source (3) in a measurement section (2);

intercepting light (14), which is transmitted through the service fluid in the measurement section (2) and/or which emanates from the same due to a fluorescent effect, by an opto-receiver device (5), the intensity of the light being influenced by the at least one indicator;

generating at least one measurement signal (8, 9) indicative of the intensity of the light impinging on the opto-receiver;

evaluating the at least one measurement signal (8, 9) in an evaluation unit (10) and comparing it to stored values.

It is advantageous in this context that the signal derived from the evaluation of the measurement signals may be further utilized in the machine. For example, the identity of or other information pertaining to the fill fluid may be automatically determined and further processed, for example in the on-board computer. Thus, in the event that an inappropriate service fluid is poured in, the machine is prevented from starting up or its operating range is limited to the point where there is no risk of damage. In addition, on the basis of the generated signals, the replacement interval for the service fluid may be calculated or adapted as a function of the fill fluid.

The at least one indicator is advantageously a fluorescing dye which is excited by the light source in the measurement section to a fluorescent radiation, the fluorescent radiation constituting at least one portion of the light intercepted by the opto-receiver.

A further improvement is achieved in that the service fluid contains at least two indicators that are active in different frequency regions and in that the indicators, in particular the concentrations thereof, are detected by at least two sensors of the opto-receiver that are sensitive in the different frequency regions.

The present invention also provides that the measurement signal(s) generated by the opto-receiver correlate with the concentration of the at least one indicator in the service fluid.

In an especially beneficial manner, one of the indicators of the service fluid forms a reference indicator on whose basis the opto-receiver generates a reference signal. This makes it possible to facilitate the evaluation of the measurement signals, in particular.

Another refinement of this inventive idea provides that the evaluation unit evaluate the at least one measurement signal on the basis of the ratio of the intensity of the at least one measurement signal to the intensity of the reference signal. This enables the indicator concentrations in the service fluid to be reliably determined, even under variable conditions, such as a fluctuating degree of filling of the measurement section with service fluid. In this connection, to determine the ratio of the indicators, it suffices to establish a relation between the measurement signal(s) and the reference signal. The evaluation is especially simple when the reference indicator is present in an always constant concentration.

A further improvement is achieved when the evaluation unit assigns a quality signal to the at least one measurement signal. This may be accomplished, for example, by comparing the concentration levels of the various indicators determined by the measurement signals to a table or value matrix, in which specific qualities of or other information pertaining to the service fluid are assigned in each instance to combinations of concentration levels of indicators. In this context, the evaluation unit may be integrated in the on-board computer of a motor vehicle, for example.

A further improvement is achieved when the quality signal is used for automatically determining the time for the next service fluid replacement. Thus, for the first time, the quality and origin of the fill fluid may be considered in the calculation or adaptation of the service interval or service fluid replacement.

BRIEF DESCRIPTION OF THE DRAWINGS

Other objectives, features, advantages arid possible applications of the present invention are derived from the following description of exemplary embodiments which makes reference to the drawing. All of the described and/or illustrated features constitute the subject matter of the present invention, either alone or in any combination.

In the drawing:

FIG. 1 schematically depicts a device for automatically detecting at least one indicator contained in a liquid service fluid during the process of filling a machine with the service fluid.

DETAILED DESCRIPTION

Figure 1:
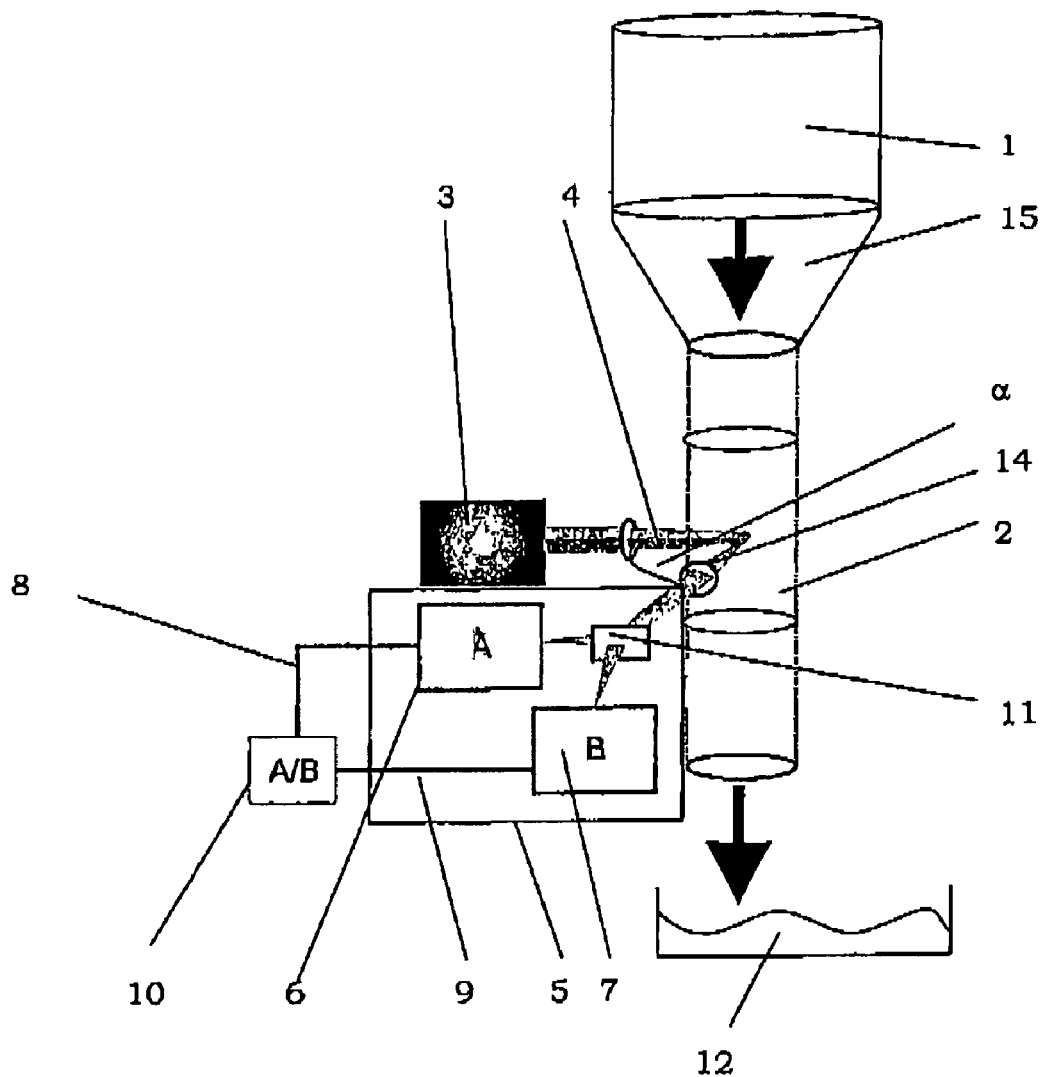
FIG. 1: is a schematic representation of a device according to the present invention.

The device has a filler tube 1 for pouring in the service fluid. In the present Application, any component that permits or facilitates the process of filling service fluid into the machine is considered to be a filler tube, regardless of its cross-sectional shape or the ratio between its diameter and length. In particular, the filler tube may be designed to be round or angular. In the illustrated specific embodiment, oblong filler tube 1 has a circular cross section. The filler tube of the device is designed and positioned in such a way that the fill fluid arrives directly or indirectly through filler tube 1 into service fluid supply 12, for example the oil sump of the machine.

In addition, the device has a measurement section 2 made of a translucent material. In the embodiment illustrated in FIG. 1, this is formed from a tubular section made of clear plastic or glass, for example. Measurement section 2 is at least partially filled with or traversed by the flow of the service fluid when filling the same into filler tube 1. It suffices in this context when only a portion of the fill fluid flows through measurement section 2 for measuring purposes.

The device according to the present invention also has a light source 3 which radiates onto measurement section 2 and is directed at the same. The light emanating from light source 3 may be a collimated beam 4 which is focused in particular at the middle of measurement section 2.

The device according to the present invention also has an opto-receiver 5. Impinging thereon is the light that is transmitted through the service fluid when the service fluid flows through measurement section 2 and/or emanates from the service fluid due to a fluorescent effect (light 14).

Illustrated opto-receiver 5 has two light sensors 6, 7 whose frequency regions are distinct from one another. Light sensors 6, 7 have different spectral sensitivity maxima which are adapted to the indicators that are used. In this manner, the presence and/or the concentration of an indicator in the service fluid may be determined by one light sensor 6, 7. In addition to the two sensors shown, other sensors may be provided, whereby one single sensor may also suffice in accordance with the present invention.

Using light sensors 6, 7, opto-receiver 5 generates in particular a plurality of measurement signals. Illustrated in FIG. 1 are a measurement signal 8 of light sensor 6 and a measurement signal 9 of light sensor 7. PIN diodes, in particular, may be employed as sensors 6, 7 of opto-receiver 5. In addition, opto-receiver 5 has a beam splitter 11 through which incoming light is uniformly distributed over light sensors 6, 7.

FIG. 1 also shows an evaluation unit 10 in which the at least one measurement signal 8, 9 of opto-receiver 5 is evaluated.

Light source 3 and opto-receiver 5 are oriented to measurement section 2 of filler tube 1 of the machine and positioned at an angle α of 0 to 170 degrees around measurement section 2. In this connection, an angle of 30 to 140 degrees, preferably of 60 to 120 degrees has proven to be particularly effective. If the intention is to determine the indicators and the concentrations thereof in the service fluid not by fluorescence measurement, but rather by absorption measurement, then opto-receiver 5 is positioned directly opposite light source 3, thus, in particular, at an angle α of 180° to the same.

In the embodiment of the present invention illustrated in FIG. 1, in the direction of flow upstream of measurement section 2, filler tube 1 has a section 15 of a reduced cross-sectional area. Due to the narrowing of cross section, the measurement section is able to be completely filled with the service fluid.

Moreover, in addition to illustrated light source 3, other light sources may be provided, which radiate in a frequency region that is distinct from that of light source 3.

In accordance with the present invention, the light sources may be constituted very simply of LEDs and/or of laser diodes. The LEDs or laser diodes may have different wavelengths.

In accordance with the present invention, the device shown in FIG. 1 is additionally a machine, in particular the engine of a vehicle.

One, or preferably two or more different fluorescent dyes are added as indicators to the service fluids. For this, a concentration in the range of $10^{-7}$ to $10^{-9}$ mol already suffices. However, higher concentrations, in particular up to $10^{-4}$ mol may also be used. As fluorescent dyes, oil-soluble dyes from the group consisting of coumarins, fluoresceins, rhodamines, oxazines and carbocyanines or oil-soluble modifications thereof may be used. Due to the low concentration of the indicators in the service fluids, the normal properties of the service fluids are not affected or are only negligibly affected. The dye is not visible to the human eye, since it is added in very low concentrations. Alternatively or additionally to the fluorescent dyes, non-fluorescent dyes, such as diazo dyes, may also be used. In accordance with the present invention, oil-soluble dyes are used, in particular fluorescent dyes having emission maxima in the 500 to 1000 nm region.

The indicators employed are detected during the filling process in response to excitation by light sources 3, for example LEDs or laser diodes, in different wavelength regions adapted to the dyes that are used. Depending on the fluorescent dyes used, the engine oils may be excited, for example, at 370, 490 and/or 570 to 590 nm.

Light is then intercepted by the opto-receiver. When fluorescent dyes are used, light 14 emitted by the indicator due to the fluorescent effect is intercepted. When non-fluorescent dyes are used, the light that passes through the service fluid is used.

Sensors 6, 7 of opto-receiver 5 each produce a measurement signal 8, 9, which is indicative of the intensity of light 14 impinging on opto-receiver 5. Accordingly, the presence, as well as the concentration of the indicators in the service fluid may be determined by evaluation unit 10 on the basis of measurement signals 8, 9.

On the basis of a comparison of the thus ascertained concentrations or concentration levels of the various indicators, a comparison is made to the comparison values stored in a table. As a function thereof, the identity of the fill fluid is determined, and a quality signal is generated. This makes it possible to automatically ascertain the identity of the fill fluid or other information pertaining to the same and to further process the thus obtained information in a computerized operation. The information pertaining to the fill fluid may be used for calculating oil replacement intervals. In addition, in the event that a fill fluid does not meet the recommended specifications, it is possible to prevent operation of the machine or to limit its operating range.

The evaluation is rendered possible in the process in that measurement signals 8, 9 generated by opto-receiver 5 correlate with the concentration of the at least one indicator in the service fluid.

In addition, the present invention may provide that one of the indicators or dyes of the service fluid constitute a reference indicator. The idea behind this is that the reference indicator be provided either in a changing or always constant concentration in the service fluid. For example, when light sensor 6 detects the reference indicator, then measurement signal 8 derived therefrom forms the reference signal. On the other hand, light sensor 7 detects another indicator of the service fluid and, as a function of the concentration of this indicator in the service fluid, generates a measurement signal 9. Since a relation is established between measurement signal 9 and reference signal 8, the concentration of the indicator or the concentration ratio of the indicators may always be reliably determined. This may also be accomplished under fluctuating measurement conditions, for example when measurement section 2 is not completely filled with service fluid. Thus, a good measuring result may be obtained under difficult or changing conditions, for example even without a section 15 having a narrowed cross section.

In accordance with the present invention, the indicators are detected when fresh oil is filled into the machine, so that decomposition products, contamination of or chemical changes in the oil are not able to influence the detection process.

Figure 2:
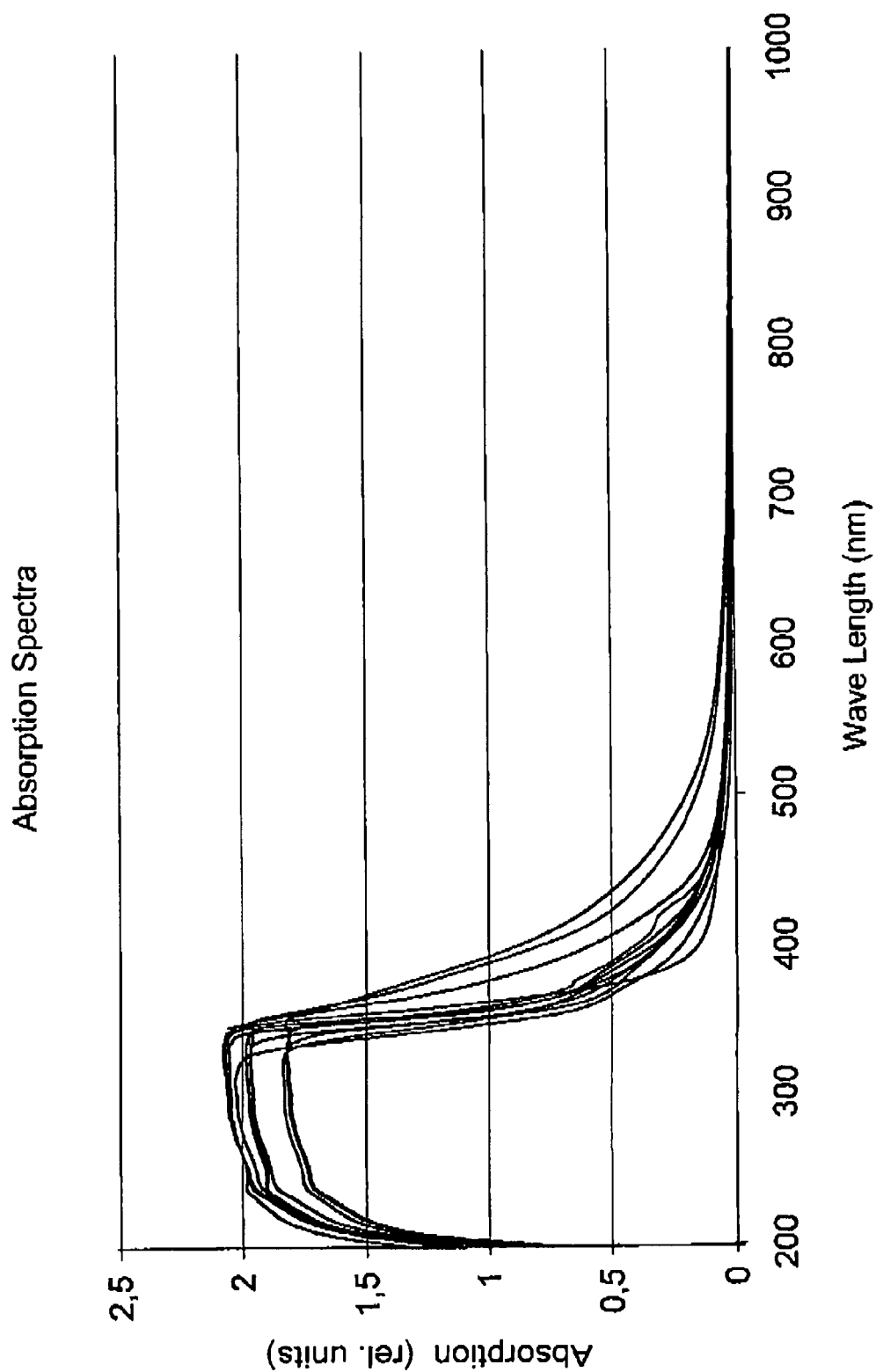
FIG. 2: illustrates the absorption spectra of various lubricating oils.

FIG. 2 shows the measured absorption spectra of a multiplicity of various engine oils. The measurements clearly show that the absorption declines sharply for all products in the region between approximately 350 and 400 nm. From a wavelength region of approximately 500 nm on, there is still only a very slight absorption, amounting to less than one fourth of that at 300 nm. For most engine oils, the fluorescence even lies substantially below this. Therefore, the use of fluorescent dyes, which absorb and emit in the 500 to 1000 nm wavelength region, presents itself in accordance with the present invention.

Example: As a service fluid, engine oil is provided with two fluorescent dyes in specified concentrations, one of which has an emission maximum at 550 nm and the other an emission maximum at 650 nm. Accordingly, light source 3 is equipped with two LEDs, which emit at 490 nm or 570 to 590 nm. In a spectrally separate process, two sensors 6, 7, designed as semiconductor detectors, detect the fluorescence produced by the indicators, with the aid of beam splitter 11 and various filters. Various engine oils are marked using different dye mixture ratios of, for example, 1:10, 2:10, 3:10 etc. and, respectively, 10:1, 10:2 etc. Accordingly, the engine oils may be uniquely identified on the basis of the various measurement signal ratios of 0.1, 0.2, 0.3 to 10 measured at the two detectors 6, 7. Thus, in this example, one derives 19 encoding options.

What is claimed is:

1. A machine comprising:
a device for automatically detecting at least one fluorescing and/or light-absorbing indicator contained in a liquid service fluid during a process of filling the service fluid into the machine, the device including a filler tube for the service fluid, the service fluid to be poured in reaching a service fluid supply of the machine through the filler tube, and further including a measurement section made of a translucent material, the measurement section at least partially filled with or traversed by a flow of the service fluid when filling the service fluid into the filler tube, the device further including at least one light source radiating onto the measurement section and an opto-receiver onto which the light impinges, the light being transmitted through the service fluid when the service fluid flows through the measurement section and/or emanating from the indicator due to a fluorescent effect, and which generates at least one measurement signal as a function of an intensity of the light impinging on the opto-receiver, the device including an evaluation unit evaluating at least one measurement signal of the opto-receiver;
wherein the filler tube leads into the measurement section.

2. The machine as recited in claim 1 wherein the opto-receiver has at least two light sensors whose frequency regions are distinct from one another, and which each generate one measurement signal.

3. The machine as recited in claim 1 wherein the light source and the opto-receiver are oriented to the measurement section and are positioned around the same at an angle of 0° to 170°.

4. The machine as recited in claim 1 wherein, in a direction of flow upstream of the measurement section, the filler tube has a reduced cross-sectional area in the section leading into the measurement section.

5. The machine as recited in claim 1 wherein the measurement section includes a measuring tube leading directly or indirectly into the service fluid supply of the machine.

6. The machine as recited in claim 1 wherein a plurality of light sources are provided, which radiate in frequency regions that are distinct from one another.

7. The machine as recited in claim 6 wherein the light sources are constituted of LEDs and/or of laser diodes having different wavelengths.

8. The machine as recited in claim 1 wherein the machine is an engine of a vehicle.

9. The machine as recited in claim 1 wherein the service fluid is lubricating oil, engine oil or hydraulic oil.

10. A method for automatically detecting at least one fluorescing and/or light-absorbing indicator contained in a liquid service fluid during the process of filling the service fluid into a machine through a device integrated in the machine, the method comprising the following steps:
filling the liquid service fluid to be detected into a filler tube, through which the service fluid arrives in the service fluid supply of the machine, and the liquid service fluid at least partially filling or flowing through a measurement section;
irradiating the liquid service fluid in the measurement section by at least one light source;
intercepting the light transmitted through the service fluid in the measurement section and/or emanating from the indicator contained in the same due to a fluorescent effect, by an opto-receiver, an intensity of the light being influenced by the at least one indicator or the concentration thereof,
generating at least one measurement signal indicative of the intensity of the light impinging on the opto-receiver; and
evaluating the at least one measurement signal in an evaluation unit and comparing the measurement signal to stored values.

11. The method as recited in claim 10 wherein the at least one indicator is a fluorescing dye which is excited by the light source in the measurement section to a fluorescent radiation; and the fluorescent radiation constitutes at least one portion of the light intercepted by the opto-receiver.

12. The method as recited in claim 10 wherein the service fluid contains at least two indicators that are active in different frequency regions; and the indicators are detected by at least two sensors of the opto-receiver that are sensitive in the different frequency regions.

13. The method as recited in claim 12 wherein concentrations of the indicators.

14. The method as recited in claim 10 wherein the measurement signal generated by the opto-receiver correlates with a concentration of the at least one indicator in the service fluid.

15. The method as recited in claim 10 wherein one of the indicators of the service fluid forms a reference indicator on whose basis the opto-receiver generates a reference signal.

16. The method as recited in claim 15 wherein the evaluation unit evaluates the at least one measurement signal on the basis of a ratio of the intensity of the at least one measurement signal to the intensity of the reference signal.

17. The method as recited in claim 10 wherein the evaluation unit assigns a quality signal to the at least one measurement signal.

18. The method as recited in claim 17 wherein the quality signal is used for automatically determining a time for the next service fluid replacement.

19. The method as recited in claim 10 wherein the machine is an engine of a vehicle.

20. The method as recited in claim 10 wherein the service fluid is lubricating oil, engine oil or hydraulic oil.

* * * * *